United States Patent [19]

Crosby et al.

[11] Patent Number: 5,851,180
[45] Date of Patent: Dec. 22, 1998

[54] TRACTION-INDUCING COMPRESSION ASSEMBLY FOR ENHANCED TISSUE IMAGING

[75] Inventors: Peter Andrew Crosby, Greenwood Village, Colo.; Ascher Shmulewitz, Mercer Island, Wash.

[73] Assignee: United States Surgical Corporation, Norwalk, Conn.

[21] Appl. No.: 680,560

[22] Filed: Jul. 12, 1996

[51] Int. Cl.⁶ .................................................. A61B 06/04
[52] U.S. Cl. ........................................... 600/407; 378/37
[58] Field of Search ........................ 128/653.1, 660.01, 128/660.09, 915; 378/37, 177, 195, 196, 197, 204, 208; 606/130; 600/407, 437, 445

[56] References Cited

U.S. PATENT DOCUMENTS

| | | |
|---|---|---|
| 3,765,403 | 10/1973 | Brenden . |
| 3,971,950 | 7/1976 | Evans et al. . |
| 3,991,316 | 11/1976 | Schmidt et al. . |
| 4,465,069 | 8/1984 | Barbier et al. . |
| 4,469,106 | 9/1984 | Harui . |
| 4,485,819 | 12/1984 | Igl . |
| 4,497,325 | 2/1985 | Wedel . |
| 4,501,278 | 2/1985 | Yamaguchi et al. . |
| 4,527,569 | 7/1985 | Kolb . |
| 4,541,436 | 9/1985 | Hassler et al. . |
| 4,545,385 | 10/1985 | Pirschel . |
| 4,573,180 | 2/1986 | Summ ........................................ 378/37 |
| 4,579,123 | 4/1986 | Chen et al. . |
| 4,583,538 | 4/1986 | Onik et al. . |

(List continued on next page.)

FOREIGN PATENT DOCUMENTS

| | | |
|---|---|---|
| 105 812 | 4/1984 | European Pat. Off. . |
| 483 005 | 4/1992 | European Pat. Off. . |
| 581 704 | 2/1994 | European Pat. Off. . |
| 25 35 576 | 1/1975 | Germany . |
| 32 26 976 | 2/1983 | Germany . |
| 32 22 053 | 12/1983 | Germany . |
| 32 27 624 | 1/1984 | Germany . |
| 34 05 537 | 8/1985 | Germany . |
| 34 47 444 | 7/1986 | Germany . |
| 40 37 387 | 5/1992 | Germany . |
| 896 539 | 4/1980 | U.S.S.R. . |

(List continued on next page.)

OTHER PUBLICATIONS

Magnusson, A., "New Stereotactic Instrument Facilitates Computer Tomographically Guided Punctio", Läkartidningen, vol. 86, No. 21, pp. 1885–1886, 1888 (1988).

Gardineer et al., "Video–photographic System for Rapid Inexpensive Unit Recording and Flexible Replay of Real–time Ultrasonic Imaging of the Breast", SPIE vol. 273, Appln. of Optical Instrumentation in Medicine IX, pp. 343–347 (1981).

Bruno D. Fornage, MD et al., Breast Masses: US–Guided Fine–Needle Aspiration Biopsy[1], Radiology, 162:409–414 (1987).

B.D. Fornage, MD et al., "Ultrasound–Guided Needle Biopsy of the Breast and Other Interventional Procedures", vol. 30, No. 1, pp. 167–185 (Jan. 1992).

(List continued on next page.)

*Primary Examiner*—Marvin M. Lateef
*Assistant Examiner*—Shawna J. Shaw

[57] ABSTRACT

Apparatus and methods are provided for compressing biological tissue for use with a radiographic or sonographic imaging system that enhances imaging of the tissue near a patient's chest wall. The apparatus includes a compression assembly having first and second compression surfaces, and structure for positioning the first compression surface relative to the second compression surface so that the first and second compression surfaces experience a lateral translation as they move towards one another. In addition the first and second compression surfaces may be tilted slightly relative to a plane orthogonal to the patient's chest wall to enhance the traction effect and to provide partial imaging within the patient's chest wall.

20 Claims, 3 Drawing Sheets

U.S. PATENT DOCUMENTS

| | | |
|---|---|---|
| 4,592,352 | 6/1986 | Patil . |
| 4,599,738 | 7/1986 | Panetta et al. . |
| 4,608,989 | 9/1986 | Drue . |
| 4,613,122 | 9/1986 | Manabe . |
| 4,613,982 | 9/1986 | Dornheim et al. .......................... 378/37 |
| 4,618,213 | 10/1986 | Chen . |
| 4,618,973 | 10/1986 | Lasky . |
| 4,625,555 | 12/1986 | Fujii . |
| 4,671,292 | 6/1987 | Matzuk . |
| 4,681,103 | 7/1987 | Boner et al. . |
| 4,686,997 | 8/1987 | Oloff et al. . |
| 4,722,346 | 2/1988 | Chen . |
| 4,727,565 | 2/1988 | Ericson . |
| 4,733,661 | 3/1988 | Palestrant . |
| 4,735,215 | 4/1988 | Goto et al. . |
| 4,750,487 | 6/1988 | Zanetti . |
| 4,774,961 | 10/1988 | Carr ......................................... 128/736 |
| 4,784,134 | 11/1988 | Arana . |
| 4,791,934 | 12/1988 | Brunnett . |
| 4,821,727 | 4/1989 | Levene et al. . |
| 4,844,080 | 7/1989 | Frass et al. . |
| 4,862,893 | 9/1989 | Martinelli . |
| 4,869,247 | 9/1989 | Howard, III et al. . |
| 4,875,478 | 10/1989 | Chen . |
| 4,890,311 | 12/1989 | Saffer . |
| 4,898,178 | 2/1990 | Wedel . |
| 4,899,756 | 2/1990 | Sonek . |
| 4,911,173 | 3/1990 | Terwilliger . |
| 4,930,143 | 5/1990 | Lundgren et al. . |
| 4,940,061 | 7/1990 | Terwilliger et al. . |
| 4,944,308 | 7/1990 | Akerfeldt . |
| 4,953,558 | 9/1990 | Akerfeldt . |
| 4,962,515 | 10/1990 | Kopans . |
| 4,962,752 | 10/1990 | Reichenberger et al. . |
| 4,966,152 | 10/1990 | Gäng et al. . |
| 4,981,142 | 1/1991 | Dachman . |
| 5,003,979 | 4/1991 | Merickel et al. . |
| 5,007,428 | 4/1991 | Watmough . |
| 5,029,193 | 7/1991 | Saffer ......................................... 378/37 |
| 5,056,523 | 10/1991 | Hotchkiss, Jr. et al. . |
| 5,078,142 | 1/1992 | Siczek et al. ........................ 128/653.1 |
| 5,078,149 | 1/1992 | Katsumata et al. . |
| 5,083,305 | 1/1992 | Tirelli et al. .............................. 378/37 |
| 5,095,910 | 3/1992 | Powers . |
| 5,099,503 | 3/1992 | Strömmer . |
| 5,107,843 | 4/1992 | Aarnio et al. . |
| 5,113,420 | 5/1992 | Davis, Jr. et al. . |
| 5,158,088 | 10/1992 | Nelson et al. . |
| 5,199,056 | 3/1993 | Darrah ...................................... 378/37 |
| 5,205,297 | 4/1993 | Montecalvo et al. . |
| 5,219,351 | 6/1993 | Teubner et al. . |
| 5,260,871 | 11/1993 | Goldberg . |
| 5,262,468 | 11/1993 | Chen . |
| 5,273,435 | 12/1993 | Jacobson . |
| 5,280,427 | 1/1994 | Magnusson et al. . |
| 5,305,365 | 4/1994 | Coe ........................................... 378/37 |
| 5,318,028 | 6/1994 | Mitchell et al. . |
| 5,361,768 | 11/1994 | Webler et al. . |
| 5,379,769 | 1/1995 | Ito et al. . |
| 5,386,447 | 1/1995 | Siczek ....................................... 378/37 |
| 5,396,897 | 3/1995 | Jain et al. . |
| 5,411,026 | 5/1995 | Carol . |
| 5,415,169 | 5/1995 | Siczek et al. . |
| 5,426,685 | 6/1995 | Pellegrino et al. . |
| 5,433,202 | 7/1995 | Mitchell et al. . |
| 5,447,154 | 9/1995 | Cinquin et al. . |
| 5,450,851 | 9/1995 | Hancock . |
| 5,474,072 | 12/1995 | Shmulewitz . |
| 5,479,927 | 1/1996 | Shmulewitz ...................... 128/660.09 |
| 5,487,387 | 1/1996 | Trahey et al. . |
| 5,488,952 | 2/1996 | Schoolman . |
| 5,499,989 | 3/1996 | LaBash . |
| 5,506,877 | 4/1996 | Niklason et al. . |
| 5,522,787 | 6/1996 | Evans . |
| 5,524,636 | 6/1996 | Sarvazyan et al. . |
| 5,594,769 | 1/1997 | Pellegrino et al. ........................ 378/37 |
| 5,595,177 | 1/1997 | Mena et al. . |
| 5,603,326 | 2/1997 | Richter . |
| 5,609,152 | 3/1997 | Pellegrino et al. . |
| 5,640,956 | 6/1997 | Getzinger et al. . |
| 5,660,185 | 8/1997 | Shmulewitz et al. . |
| 5,664,573 | 9/1997 | Shmulewitz et al. . |

FOREIGN PATENT DOCUMENTS

| | | |
|---|---|---|
| 2 094 590 | 9/1982 | United Kingdom . |
| WO 88/08272 | 11/1988 | WIPO . |
| WO 89/11248 | 11/1989 | WIPO . |
| WO 94/21189 | 9/1994 | WIPO . |
| WO 95/11627 | 5/1995 | WIPO . |

OTHER PUBLICATIONS

Darla Haight et al., "Radiologists Spread Their Wings: A Look at the Possibilities in STereotactic Breast Biopsy", Admin. Rad. J., pp. 87–89 (Nov. 1987).

E. Azavedo et al., "Stereotactic Fine–Needle Biopsy in 2594 Mammographically Detected Non–Palable Lesions", The Lancet, pp. 1033–1036 (May 1989).

Eva Rubin, MD, "Breast Cancer in the 90's", Applied Radiology, pp. 23–26 (Mar. 1993).

Ellen B. Mendelson, MD, "Ultrasound Secures Place in Breast Ca Management", Diagnostic Imaging, pp. 120–129 (Apr. 1991).

Ferris H. Hall, MD, "Mammographic Second Opinions Prior to Biopsy of Nonpalpable Beast Lesions", Arch Surg, vol. 125, pp. 298–299 (Mar. 1990).

Gunilla Svane, MD., "Stereotactic Needle Biopsy", Dept. of Dianostic Radioloyg at the Karolinska Hospital, Stockholm, Sweden (1987).

Gillian Newstead, MD., "When and When Not to Biopsy the Breast", Diagnostic Imaging, pp. 111–116, (Mar. 1993).

Ingvar Andersson, MD, "Medical Radiography and Photography", vol. 62, No. 2, pp. 2–41 (1986).

Jan Bolmgren, et al., "Stereotaxic Instrument for Needle Biopsy of the Mamma", (Sweden) J. Radiology, 129:121–125 (Jul. 1977).

Kambiz Dowlatshahi, MD, Breast Care: "The Needle Replaces The Knife" (Exploring Sterotactic Guided Needle Biopsy), Admin. Radiology, pp. 28–31 (Jun. 1989).

K. Dowlatshahi, MD, "Nonpalpable Breast Tumors: Dianosis with Stereotaxic Localization and Fine–Needle Aspiration[1]", Radiology 170, No. 2, pp. 427–433 (Feb. 1989).

Ralph Mösges et al., "Multimodal Information for Computer–Integrated Surgery", Mösges & Lavallée: Multimodal Information for CIS/Data Acquisition & Segmentation, pp. 5–19.

Rachel F. Brem, MD et al., "Template–guided Breast US[1]", Radiology 184:872–874 (Sep. 1992).

Steve H. Parker, MD et al., "Percutaneous Large–Core Breast Biopsy: A Multi–institutional Study[1]", Radiology vol. 193, No. 2, pp. 359–364 (Nov. 1994).

S.H. Parker, MD et al., "Large–Core Breast Biopsy Offers Reliable Diagnosis", Diagnostic Imaging, 8 pages (Oct. 1990).

S.H. Parker, MD et al., "US–guided Automated Large–Core Breast Biopsy[1]", Radiology, 187:507–511 (May 1993).

P.N.T. Wells et al., "Tumor detection by ultrasonic Doppler blood–flow signals", Ultrasonics, pp. 231–232 (Sep. 1977).

Valerie P. Jackson, MD "The Role of US in Breast Imaging[1]", Radiology 177:305–311 RSNA (Nov. 1990).

W. Phil Evans, MD et al., "Needle Localization and Fine–Needle Aspiration Biopsy of Nonpalpable Breast Lesions with use of Standard and Stereotactic Equipment", Radiology, 173:53–56 (1989).

William F. Conway, MD et al., "Occult Breast Masses: Use of a Mammographic Localizing Grid for US Evaluation[1]", Radiology, 181:143–146 (1991).

TRACTION-INDUCING COMPRESSION ASSEMBLY FOR ENHANCED TISSUE IMAGING

BACKGROUND OF THE INVENTION

This invention relates to apparatus and methods for conducting an examination of biological tissue, especially breast tissue, that provides enhanced imaging of the tissue. In particular, the present invention provides an assembly for inducing traction in breast tissue while the tissue is being compressed, thereby drawing the tissue away from the chest wall.

Apparatus and methods are known for imaging the internal structure of body tissue, for example, using radiographic and sonographic techniques, to identify tumorous masses and other abnormalities. Such imaging capability has provided significant benefits in the early diagnosis of breast cancer.

In radiographic systems, breast tissue typically is compressed between a compression plate and a diffraction grid to form a substantially uniform thickness. The compressive forces applied by the system assist in spreading the internal structures of the tissue, immobilize the tissue against movement during exposure of the X-ray film or imaging elements, and permit the use of lower dosages of X-rays to obtain an image.

In addition, flattening the tissue to a uniform thickness enables most of the area of the breast to be imaged with a single exposure, so that only the reduced-thickness portions at the periphery of the breast are overexposed. Typically, the periphery of the breast is imaged using a second, lower dose of radiation than is used for the uniform thickness of the breast.

In sonographic systems, such as Brenden U.S. Pat. No. 3,765,403, where the imaging is conducted using ultrasound technology, the breast tissue typically is suspended in a water bath. In such systems the tissue is not compressed, but is merely urged into the water bath by gravity and the patient's weight. Alternatively, in the system described in commonly assigned U.S. Pat. No. 5,474,072, the breast is compressed between first and second compression surfaces, so that the breast is flattened to a uniform thickness for both radiographic and ultrasound imaging.

A drawback common to both previously known radiographic and sonographic imaging systems is the inability to image tissue in the vicinity of the chest wall. In the case of radiographic systems and the sonographic system described in the above-mentioned U.S. Pat. No. 5,474,072, compressive forces applied to the breast tissue to flatten it to a uniform thickness tend to force tissue out from between the compression surfaces. Consequently, internal breast structures near the patient's chest wall are forced inward through the patient's chest wall, and therefore are difficult to bring within the field of the radiographic or sonographic imaging device. Alternatively, in water bath sonographic systems, only gravity, and perhaps the patient's body weight, are available to urge the internal tissue structures within the field of the ultrasound scanner.

An attempt to overcome the above disadvantages of previously known compression arrangements is provided in Kopans U.S. Pat. No. 4,962,515. That patent describes a compression assembly comprising upper and lower compression plates, each of the upper and lower compression plates including a ridge disposed adjacent the patient's chest wall. The ridge serves to grip the patient's tissue near the chest wall and counteract the tendency of compressive forces to push the tissue inward through the patient's chest wall. Such a system has two perceived drawbacks, however. First, the tissue in the vicinity of the ridges is expected to have a localized reduction in thickness in the region adjacent the breast wall which is expected to become overexposed, in a manner similar to that of the breast periphery. Second, the additional thickness of the compression surfaces caused by the present of the ridges near the chest wall is expected to interfere with the ability to image tissue between or proximally (with respect to the patient's chest) of the ridge location.

Another arrangement for enhancing imaging of breast tissue is described in Niklason et al. U.S. Pat. No. 5,506,877. In the arrangement described in that patent a movable upper breast paddle is described which attempts to mimic the contours of the breast. The paddle is arranged so as to pivot along a line adjacent to the patient's chest wall. A drawback of this system is that it does not improve imaging near the patient's chest wall. Rather, the location of the pivot point near the chest wall is expected only to exacerbate the difficulty in providing accurate imaging near the chest wall, since the paddle is expected to exert a lateral compressive load on the tissue forcing it inward through the patient's chest wall.

In view of the foregoing, it would be desirable to provide a compression assembly for enhancing imaging of internal tissue structures in the vicinity of a patient's chest wall.

It would further be desirable to provide a compression assembly for use in radiographic or sonographic imaging systems that provides enhanced imaging in the vicinity of a patient's chest wall without reducing the thickness of the compressed tissue substantially from that of adjacent tissue regions, thus reducing overexposure of the tissue near the chest wall.

It would also be desirable to provide a compression assembly for use in radiographic and sonographic systems that does not interfere with the capability of the system to provide partial imaging within the patient's chest wall.

SUMMARY OF THE INVENTION

In view of the foregoing, it is an object of this invention to provide a compression assembly for enhancing imaging of internal tissue structures in the vicinity of a patient's chest wall.

It is another object of the present invention to provide a compression assembly for use in radiographic or sonographic imaging systems that provides enhanced imaging in the vicinity of a patient's chest wall without reducing the thickness of the compressed tissue substantially from that of adjacent tissue regions, thus reducing overexposure of the tissue near the chest wall.

It is yet another object of this invention to provide a compression assembly for use in radiographic and sonographic systems that does not interfere with the capability of the system to provide at least partial imaging within the patient's chest wall.

These and other objects of the invention are accomplished in accordance with the principles of the invention by providing a compression assembly that induces a state of traction in a biological tissue, especially breast tissue, while the tissue is being compressed to a substantially uniform or tapered thickness. In a preferred embodiment, the compression assembly includes upper and lower compression surfaces that are displaced laterally when moved perpendicularly with respect to one another. In particular, an upper compression surface is arranged to be displaced laterally in a distal direction when moved towards the lower compression surface, thereby drawing the tissue in contact with the upper compression surface away from the patient's chest wall as the tissue is being flattened between the compression surfaces. To assist this traction effect, one or both of the compression surfaces may have slightly roughened or tacky surface to grip the tissue in contact therewith.

In an alternative embodiment for use with an ultrasound scanner, as described for example, in the above-mentioned U.S. Pat. No. 5,474,072, the lower compression plate is angled relative to a plane parallel with the patient's chest wall, so that the ultrasound signals can penetrate the patient's chest wall to provide partial imaging of internal tissue structures that extend within the patient's chest line.

Brief Description of the Drawings

Further features of the invention, its nature and various advantages will be more apparent from the accompanying drawings and the following detailed description of the preferred embodiments, in which.

DETAILED DESCRIPTION OF THE INVENTION

In overview, the present invention is directed to a compression assembly for use in radiographic, sonographic, or similar type imaging systems, which enhances imaging of biological tissue in the vicinity of the patient's body wall. In particular, when applied to breast imaging technology, the present invention induces traction in breast tissue as the tissue is compressed, thereby drawing a portion of the internal tissue structure adjacent to the patient's chest wall within the imaging field. While illustrative embodiments are described hereinbelow for use in conducting X-ray and ultrasound imaging of breast tissue, other applications of the present invention to imaging of biological tissue will be apparent to one of skill in the art.

Figure 1:
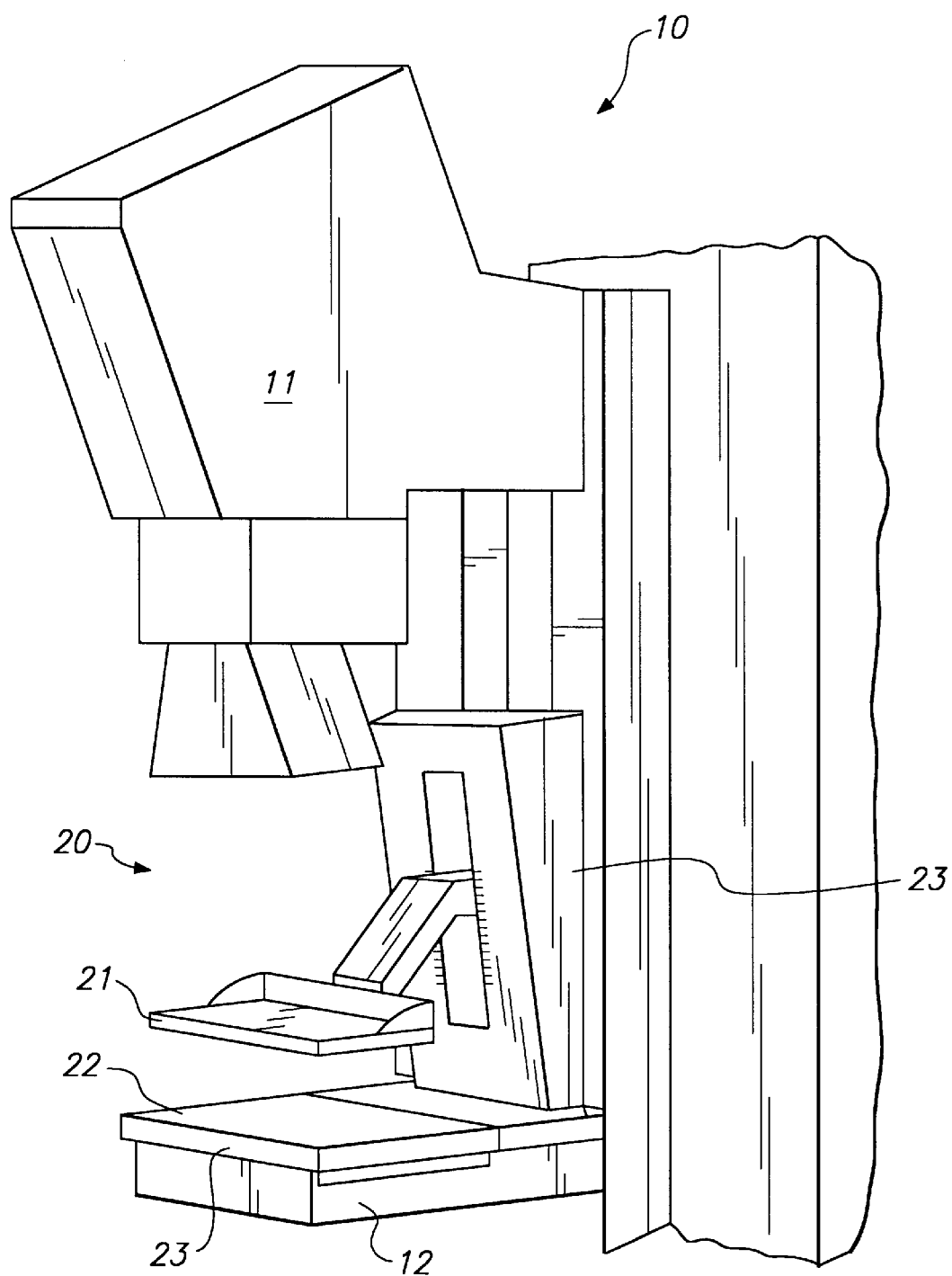
FIG. 1 is a perspective view of mammography apparatus constructed in accordance with the principles of the present invention.

Referring to FIG. 1, an illustrative embodiment of mammography apparatus 10 including a compression assembly 20 constructed in accordance principles of the present invention is described. Mammography apparatus 10 comprises X-ray generating device 11, compression assembly 20 and diffraction grating and film cassette holder 12. Compression assembly 20 includes upper compression plate 21, lower compression surface 22 having proximal edge 23 and support assembly 30 that enables upper compression plate 21 to be displaced rearwardly from proximal edge 23 when upper compression plate is lowered towards lower compression surface 22.

Figure 2:
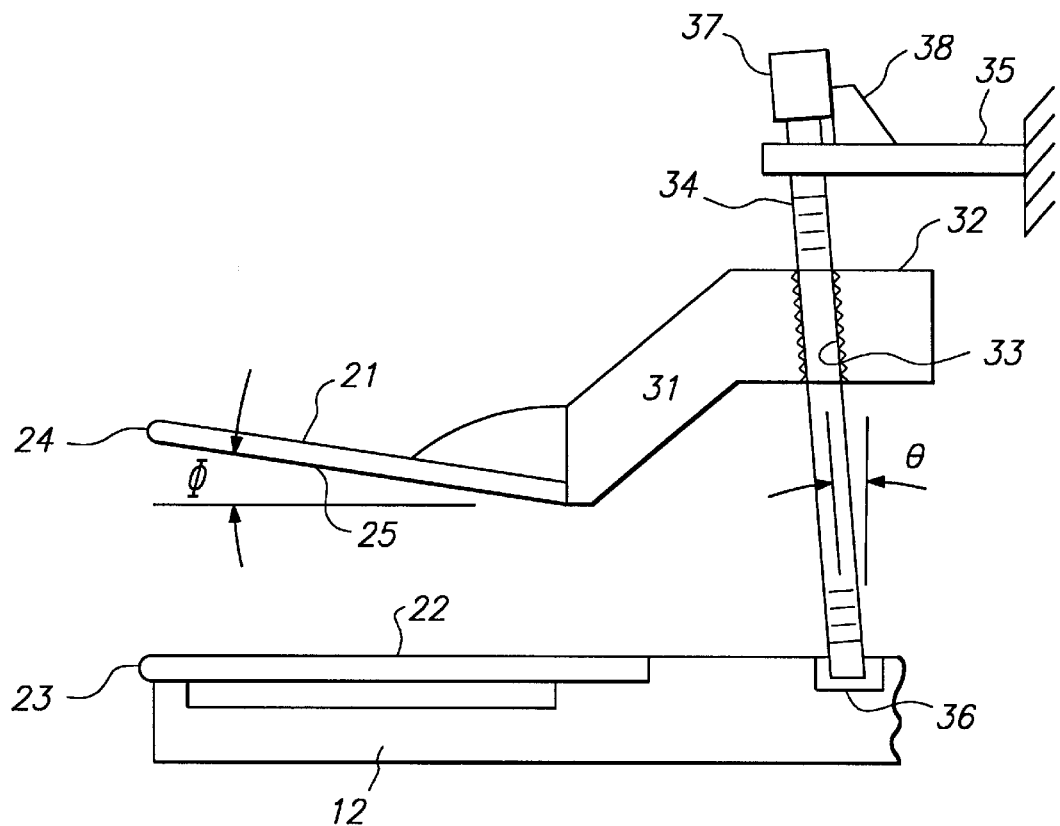
FIG. 2 is a partial elevation side view of the compression assembly of the mammography apparatus of FIG. 1.

Referring now to FIG. 2, an illustrative arrangement of support assembly 30 of FIG. 1 is shown in which the exterior housing of support assembly 30 has been removed to reveal a screw-type drive arrangement for upper compression plate 21. Other drive means, both motor-driven and manual, will occur to those of skill in the art, and the drive arrangement provided in FIG. 2 is intended to be illustrative only.

Upper compression plate 21 is attached to support arm 31 which is in turn coupled to screw block 32. Screw block 32 includes threaded bores 33 through which two threaded bars 34 pass (only one of which is visible in FIG. 2). Threaded bars 34, which provide vertical positioning means for screw block 32, are journaled between support block 35 and thrust bearing 36. Motor 37 is mounted to support block 35 via plate 38 and coupled to threaded bars 34, so that rotation of motor 37 rotates threaded bars in threaded bores 33 of screw block 32, thereby raising or lowering support arm 31 and upper compression plate 21.

In accordance with the present invention, vertical positioning means (threaded bars 34) are canted forward from the vertical by angle $\theta$ of up to about 15 degrees, and preferably about 4 degrees. Lower surface 24 of upper compression plate 21 is also raised by angle $\Phi$, from the horizontal, of up to about 45 degrees, and preferably about 4 degrees.

The combination of angle $\theta$ of the vertical positioning means and angle $\Phi$ of lower surface 24 of upper compression plate 21 result in two effects that cause the internal structures near the patient's chest wall to be drawn into the imaging field. In particular, when upper compression plate 21 is lowered towards lower compression surface 22, proximal-most edge 24 of the upper compression plate is displaced slightly rearwardly relative to proximal edge 23 of lower compression surface 22. Rearward displacement of upper compression plate 24 with respect to lower compression surface 22, induces a state of traction in tissue disposed between the compression plates, and especially in the tissue contacting lower surface 25 of upper compression plate 21. Thus, as compression plate 21 is lowered toward lower compression surface 22, the tissue in the vicinity of the patient's chest wall is drawn between upper compression plate 21 and lower compression surface 22.

As a result of angling the upper compression plate and canting the vertical positioning means, tissue is drawn into the imaging field as the tissue is flattened to a substantially uniform or tapered thickness. Thus, the tendency in previously known compression assemblies for the compressive force to urge tissue inward through the patient's chest wall is reduced. Moreover, because the compression arrangement of the present invention does not introduce local discontinuities in the thickness of the tissue adjacent the patient's chest wall, unlike the aforementioned Kopans patent, it is expected that a single exposure will provide adequate clarity for tissue near the patient's chest wall as well as for tissue within the central portions of the imaging field.

In addition, to further enhance the above-described traction effect, one or both of lower surface 25 of upper compression plate 21 and lower compression surface 22 may include a slightly roughened or tacky surface, for example, a sheet or strip of rubber, so that the tissue adheres or is gripped by the respective surface at points of contact. For sonographic applications, such as described below, a gel pad may be used to provide this functionality.

With respect to FIG. 3, compression assembly 40 as described hereinabove is shown as modified for use with ultrasound scanner 50 for use in a sonography system. Ultrasound scanner 50 comprises housing 51 enclosing a gantry carried ultrasound transducer 53 (see FIGS. 4) or an array of piezoelectric ultrasound transducer elements as described, for example, with respect to FIGS. 3 and 7 of the aforementioned U.S. Pat. No. 5,474,072, the entirety of which is incorporated herein by reference. Alternatively, the ultrasound scanner may be manually driven, as described in concurrently filed, copending, and commonly assigned U.S. patent application Ser. No. 08/680,595. The upper surface of housing 51 forms a lower compression surface 52 against which the tissue is immobilized. As described in the above-incorporated patent, the compression surface 52 is preferably formed of a sonolucent material. A gel pad, not shown, preferably is disposed between the tissue and compression surface 52 to provide acoustic coupling therebetween.

Figure 3:
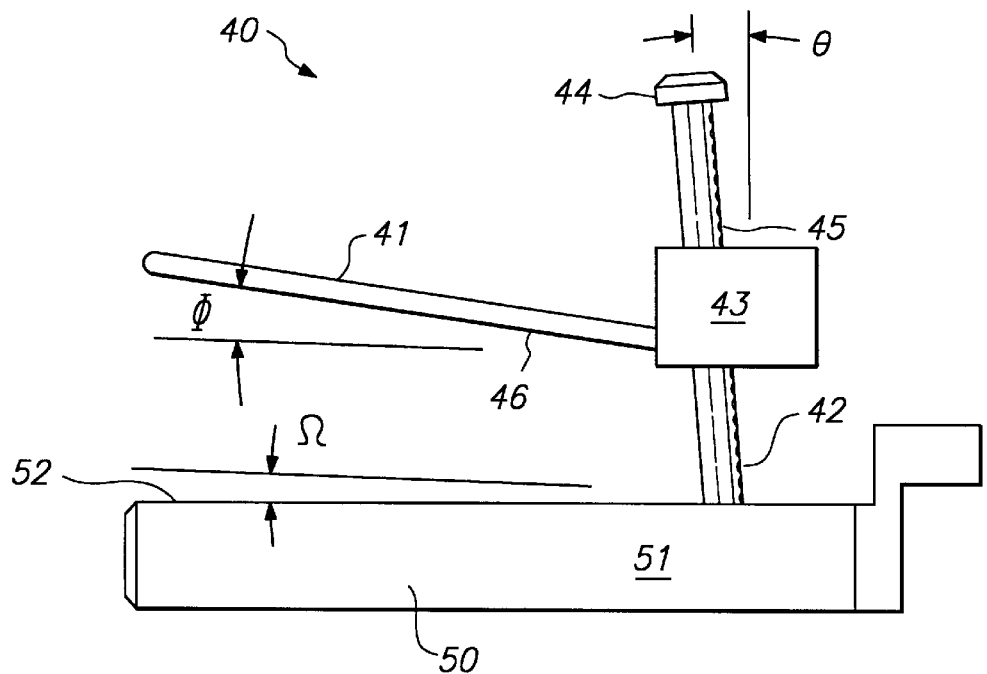
FIG. 3 is a partial elevation side view of a sonography system constructed in accordance with the principles of the present invention.

In the illustrative embodiment of FIG. 3, compression assembly 40 comprises compression surface 52 of ultrasound scanner 50, upper compression plate 41, vertical positioning bars 42 (only one of which is visible in FIG. 3), slide block 43 and top block 44. Slide block 43 is engaged with gearing 45 disposed along the rearward faces of vertical positioning bars 42 to provide a rack and pinion-type drive. A suitable motor and gearing or manual drive (neither shown) is connected to slide block 43 for driving slide block in directions substantially perpendicular to the horizontal, i.e., towards and away from compression surface 52.

In accordance with the present invention, vertical positioning bars 42 are canted forward from the vertical by angle $\theta$ of up to about 15 degrees, and preferably about 4 degrees. Lower surface 46 of upper compression plate 41 is also raised angle $\Phi$, from the horizontal, of up to about 45 degrees, and preferably about 4 degrees. In addition, compression surface 52 of housing 51 of ultrasound scanner 50 is also inclined inward towards the patient's chest wall, relative to the horizontal, by angle $\Omega$, for reasons described in greater detail hereinbelow. Angle $\Omega$ may be up to 90 degrees from the horizontal, and is preferably about 4 degrees. In one intended use of the ultrasonic scanner of the present invention, wherein the angle $\Omega$ is 90 degrees, upper compression plate 41 and vertical positioning bars 42 are removed so that compression surface 52 may be pressed directly against the patient's chest wall, for example, for imaging features within the chest wall.

Figure 4A:
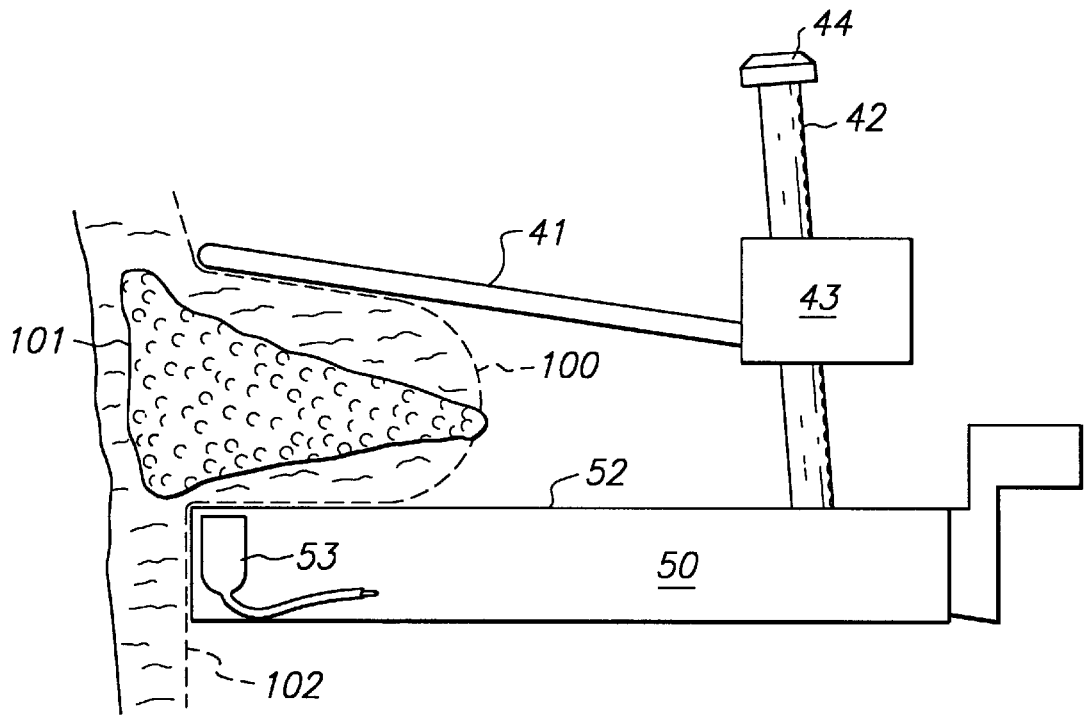
FIGS. 4A and 4B are, respectively, elevation side views of tissue disposed within the compression assembly of FIG. 3, before and after the upper compression plate is lowered to compress the tissue.
Figure 4B:
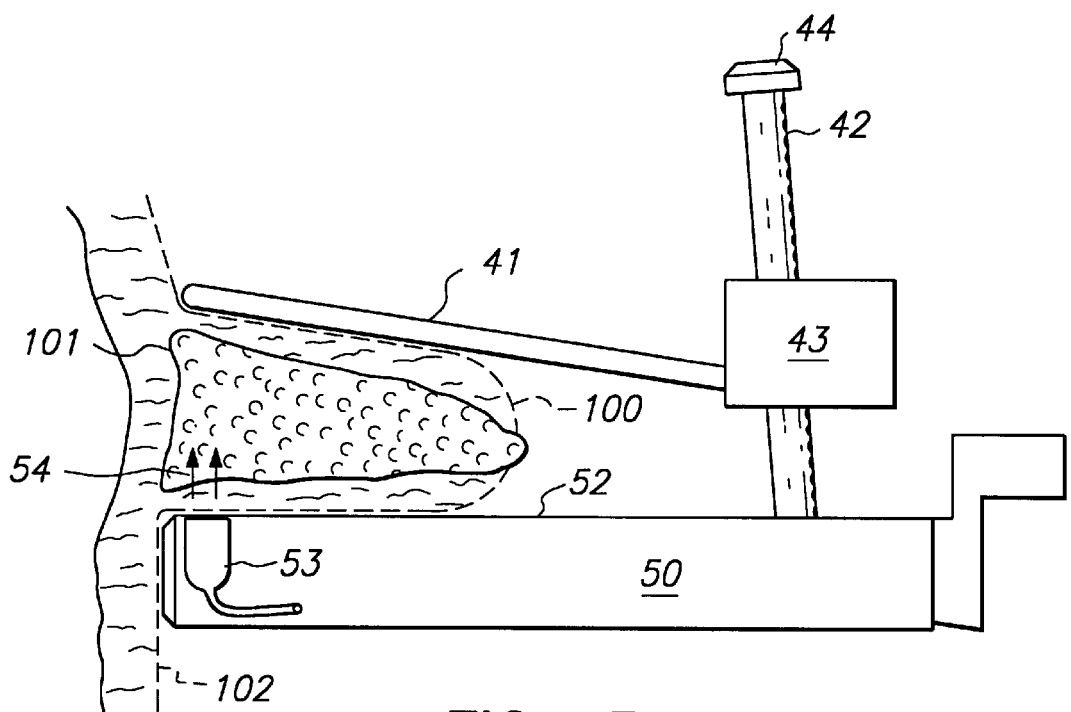

Referring now to FIGS. 4A and 4B, operation of the traction-inducing effect of compression assembly 40 is illustrated. As for the embodiment of FIG. 2, the combination of angle $\theta$ of vertical positioning bars 43 and angle $\Phi$ of lower surface 46 of upper compression plate 41 cause internal structure 101 of breast tissue 100 near the patient's chest wall 102 to be drawn into the imaging field. When upper compression plate 41 is lowered towards compression surface 52, the upper compression plate is displaced slightly rearwardly relative to compression surface 52, thereby inducing a state of traction in tissue 100 and internal structure 101 disposed therebetween.

Consequently, by angling the upper compression plate and canting the vertical positioning bars, tissue 100 and internal structure 101 are drawn into the imaging field as they are flattened to a substantially uniform or gradually tapered thickness. The tendency in previously known compression assemblies for the compressive force to urge tissue out from between the compression surfaces, and thus out of the imaging field, is reduced.

Still referring to FIGS. 4, the advantage of lowering compression surface 52 of ultrasound scanner 50 horizontal by angle $\Omega$ relative to the horizontal is now described. As depicted in FIGS. 4, ultrasound transducer 53 enclosed within ultrasound scanner housing 51 preferably is acoustically coupled to the underside of compression surface 52 via a suitable lubricious couplant, for example, glycerol. By lowering compression surface 52 from the horizontal by an angle $\Omega$, acoustic signals emanating from ultrasound transducer 53 are no longer perpendicular to the patient's chest wall 102, but will penetrate the chest wall to an extent beyond the proximal edge of upper compression plate 41, as indicated by arrows 54 in FIG. 4B. Thus, not only will the traction-inducing effect of compression assembly 40 draw tissue into the imaging field, but in addition, by angling the compression surface of the ultrasound scanner, an ultrasound image of internal structures extending partially within the patient's chest wall 102 may be imaged.

As will be appreciated by those of skill in the art, the traction-inducing compression assembly 40 of the present invention is expected to provide enhanced imaging within the field of the compression area superior to that which may be achievable using the system described in the aforementioned Kopans patent, because there are no local discontinuities in the tissue thickness which may effect exposure of the image. Further, when employed in a sonographic system, the compression arrangement of the present invention obviates the need for a ridge near the patient's chest wall, thereby eliminating material near the patient's chest wall that might interfere with imaging internal tissue structure extending partially within the patient's chest wall.

It will be understood that the foregoing is merely illustrative of the apparatus and methods of the present invention, and that various modifications can be made by those skilled in the art without departing from the scope and spirit of the invention.

What is claimed is:

1. A compression assembly for imaging biological tissue, the compression assembly for use with imaging apparatus that provides a visualization of an internal structure of the biological tissue, the compression assembly comprising:

a fixed compression surface having a fixed first proximal edge;

a second compression surface having a second proximal edge;

means for positioning the first compression surface substantially opposite and spaced apart from the second compression surface to define an imaging field, the means for positioning including means for moving the first compression surface relative to the second compression surface so that the first proximal edge moves rearwardly of the second proximal edge when the first compression surface is moved towards the second compression surface, thereby inducing traction in a biological tissue when partially inserted between the first compression surface and the second compression surface, the traction assisting in drawing the internal structure of the biological tissue within the imaging field.

2. The compression assembly as defined in claim 1 wherein the means for positioning comprises a support member connected to the first compression surface and a vertical positioning means, the vertical positioning means angled forward from a plane parallel to a patient's chest wall by an angle $\theta$.

3. The compression assembly as defined in claim 2 wherein the vertical positioning means comprises a screw-type drive.

4. The compression assembly as defined in claim 2 wherein the vertical positioning means comprises a rack and pinion-type drive.

5. The compression assembly as defined in claim 2 wherein the angle $\theta$ is less than about fifteen degrees.

6. The compression assembly as defined in claim 1 wherein the first compression surface is inclined inward towards a patient's chest wall by an angle Φ, relative to a plane orthogonal to the patient's chest wall.

7. The compression assembly as defined in claim 6 wherein the angle Φ is less than about forty-five degrees.

8. The compression assembly as defined in claim 1 wherein the second compression surface is inclined inward towards a patient's chest wall by an angle Ω, relative to a plane orthogonal to the patient's chest wall.

9. The compression assembly as defined in claim 8 wherein the angle Ω is less than ninety degrees.

10. The compression assembly as defined in claim 1 wherein at least one of the first and second compression surfaces grips tissue when tissue is disposed in contact therewith.

11. Apparatus for imaging biological tissue comprising an imaging system that provides a visualization of an internal structure of the biological tissue and a compression assembly comprising a first compression surface having a fixed first proximal edge, a second compression surface having a second proximal edge, and means for positioning the first compression surface substantially opposite and spaced apart from the second compression surface to define an imaging field, the improvement comprising:

means for moving included within the means for positioning for moving the first compression surface relative to the second compression surface so that the first proximal edge moves rearwardly of the second proximal edge as the first compression surface is moved towards the second compression surface.

12. The apparatus as defined in claim 11 wherein the means for positioning comprises a support member connected to the first compression surface and a vertical positioning means, the vertical positioning means angled forward from a plane parallel to a patient's chest wall by an angle θ.

13. The apparatus as defined in claim 11 wherein the first compression surface is inclined inward towards a patient's chest wall by an angle Φ, relative to a plane orthogonal to the patient's chest wall.

14. The apparatus as defined in claim 11 wherein the second compression surface is inclined inward toward a patient's chest wall by an angle Ω, relative to a plane orthogonal to the patient's chest wall.

15. The compression assembly as defined in claim 11 wherein at least one of the first and second compression surfaces grips tissue when tissue is disposed in contact therewith.

16. The apparatus as defined in claim 11 wherein the imaging system generates radiographic images.

17. The apparatus as defined in claim 11 wherein the imaging system generates ultrasound images.

18. A method of compressing biological tissue to a substantially uniform thickness for use with an imaging apparatus that provides a visualization of an internal structure of the biological tissue, the method comprising steps of providing a first compression surface having a fixed proximal edge;

providing a second compression surface having a proximal edge;

inserting a biological tissue between the first and second compression surfaces and in contact therewith;

translating the first compression surface so that the first proximal edge moves distally of the second proximal edge as the first compression surface is moved towards the second compression surface, thereby inducing a state of traction in the biological tissue as the biological tissue is compressed between the first compression surface and the second compression surface.

19. The method as defined in claim 18 further comprising steps of tilting the first compression surface slightly upward by an angle Φ with respect to a horizontal plane, and maintaining the first compression surface at the angle Φ during the step of translating.

20. The method as defined in claim 18 further comprising steps of tilting the second compression surface slightly downward by an angle Ω with respect to a horizontal plane, and maintaining the second compression surface at the angle Ω during the step of translating.

* * * * *